United States Patent [19]

Frenette et al.

[11] Patent Number: 4,857,659

[45] Date of Patent: Aug. 15, 1989

[54] STEREOSELECTIVE SYNTHESIS OF LEUKOTRIENE ANTAGONISTS

[75] Inventors: Richard Frenette; Jacques-Yves Gauthier, both of Laval; Robert N. Young, Senneville; Robert Zamboni, Longueuil, all of Canada; Masatoshi Kakushima, Yokohama, Japan; Thomas R. Verhoeven, Cranford, N.J.

[73] Assignee: Merck Frosst Canada, Inc., Kirkland, Canada

[21] Appl. No.: 38,814

[22] Filed: Apr. 15, 1987

Related U.S. Application Data

[63] Continuation-in-part of Ser. No. 856,910, Apr. 28, 1986, abandoned.

[51] Int. Cl.$^4$ ............................................. C07C 149/40
[52] U.S. Cl. .................................... 562/426; 562/429; 562/463
[58] Field of Search ........................ 562/426, 429, 403

[56] References Cited

FOREIGN PATENT DOCUMENTS 0104885 4/1984 European Pat. Off. .
0156233 2/1985 European Pat. Off. .

OTHER PUBLICATIONS

R. Frenette et al., J. Org. Chem., 52, 304-307, 1987.
Ann. Rpts. in Med. Chem., 19, D. M. Bailey ed., 241-251, 1984.

*Primary Examiner*—Paul J. Killos
*Attorney, Agent, or Firm*—Gabriel Lopez; Hesna J. Pfeiffer

[57] ABSTRACT

The present invention relates to a stereo-selective synthesis of leukotriene antagonists. More particularly, this invention relates to the stereo-selective synthesis of ($\beta$S,$\gamma$R) and ($\beta$R,$\gamma$S)-4-((3-(4-acetyl-3-hydroxy-2-propyl(phenoxy)propyl)-thio-$\gamma$-hydroxy-$\beta$-methylbenzenebutanoic acid, and related compounds. These compounds are useful therapeutic agents for treating allergic conditions, asthma, cardiovascular, disorders, inflammation and pain in mammals, especially humans. The compounds are also useful for inducing cytoprotection in mammals, especially humans.

3 Claims, No Drawings

1

STEREOSELECTIVE SYNTHESIS OF LEUKOTRIENE ANTAGONISTS

CROSS-REFERENCE

This is a continuation-in-part of U.S. Ser. No. 856,910, filed Apr. 28, 1986, now abandoned.

BACKGROUND OF THE INVENTION

The present invention relates to a stereoselective synthesis of leukotriene antagonists. More Particularly, this invention relates to the stereoselective synthesis of ($\beta S,\gamma R$) and ($\beta R,\gamma S$)-4-(3-(4-acetyl-3-hydroxy-2-propyl(phenoxy)propyl)-thio)-$\gamma$-hydroxy-$\beta$-methylbenzenebutanoic acid, and related compounds. These compounds are useful therapeutic agents for treating allergic conditions, asthma, cardiovascular disorders, inflammation and pain in mammals, especially humans. The compounds are also useful for inducing cytoprotection in mammals, especially humans.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$ These compounds collectively account for the biologically active material known as the slow reacting substance of anaphylaxis. See for example, Kreutner, W., et al., *Ann. Rpts. Med. Chem.*, 19, 241 (1984).

The leukotrienes are potent smooth muscle contracting agents, particularly on respiratory smooth muscle but also on other tissues (e.g., gall bladder). In addition, they promote mucous production, modulate vascular permeability changes, and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also affects other cell types such as lymphocytes and, for example, may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, Bailey, D. M., et al., *Ann. Rpts. Med. Chem.*, 17, 203 (1982).

The leukotrienes are potent spasmogens of human trachea, bronchus and lung parenchymal strips, and when administered to normal volunteers as aerosols are 3,800 times more potent than histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs.

In vitro studies have shown that antigen challenge of human lung results in the release of leukotrienes and in addition purified human mast cells can produce substantial amounts of leukotrienes. There is therefore good evidence that the leukotrienes are important mediators of human asthma.

Psoriasis is a human skin disease which affects between two and six percent of the population. There is no adequate therapy for psoriasis or related skin conditions. One of the earliest events in the development of prepapillary lesions is the recruitment of leukocytes to the skin site. Thus, it is postulated that one or more of the leukotrienes is involved in these diseases.

Leukotriene antagonists may also be used to treat or prevent mammalian (especially human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

A general method for making the compounds of Formula I and the leukotriene antagonist activity of the compounds is described in EP No. 104,885, published Apr. 4, 1984. Since there are two asymmetric atoms in the compounds of Formula I, following the general method of the above patent application results in the formation of two diastereomers, each consisting of a racemate. In the application cited above, racemic compounds are resolved by a very difficult chromatographic separation step so that the pure enantiomers can be prepared. Moreover, the racemic diasteriomers consist of one racemate which is often much more active as a leukotriene antagonist than the other one and the same is true of the two enantiomers of each racemic diasteriomer. Furthermore, the less active diasteriomer and enantiomer generally possesses the same intrinsic toxicity as the more active diasteriomer and enantioner. In addition, it can be demonstrated that the less active diasteriomer or enantiomer depresses the antagonist activity of the active diasteriomer or enantiomer at the tissue level. Thus, for three reasons it is advantageous to use the pure, more active diasteriomer or enantiomer rather than the mixed diasteriomer or racemate.

The present invention provides improved stereoselective methods of preparing the compounds of Formula I whereby the active, more desired diasteriomer is produced essentially free of the less active undesired diasteriomer. Thus, the present invention provides new and unexpected methods which greatly improve the yield of the desired product and avoids the very difficult chromatographic separation step shown in the patent application cited above.

Additionally, the present invention provides novel intermediates which are useful in improved stereoselective methods of preparing the compounds of Formula I. The use of certain of these novel intermediates leads to final product leukotriene antagonists in greater yield and at reduced cost. Moreover, among the numerous advantages over the prior art, the use of these novel intermediates results unexpectedly in a higher ratio of the active, desired diastereomer to the less active, undesired diastereomer than by use of prior art intermediates.

SUMMARY OF THE INVENTION

The present invention relates to a stereoselective synthesis of the compound of the Formula I in its racemic form:

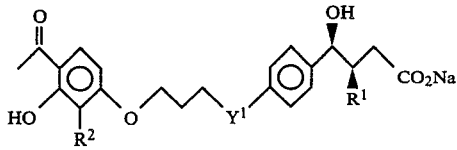

wherein:

$Y_1$ is O, S or $SO_2$; and $R^1$ and $R^2$ are independently $C^1$ to $C_6$ alkyl.

A preferred embodiment is where $R^1$ is methyl and $R^2$ is n-propyl.

The Formula I compounds and similar structural analogs have activity as antagonists of leukotriene $B_4$, and of leukotrienes $C_4$, $D_4$, $E_4$ and $F_4$, the active elements of the slow reacting substance of anaphylaxis (SRS-A).

This antagonist activity indicates that the Formula I compounds and like compositions are useful to treat, prevent, or ameliorate in mammals and especially in humans: (1) pulmonary conditions including diseases such as asthma; (2) allergies and allergic reactions such as allergic rhinitis, contact dermatitis, allergic conjunctivitis and the like; (3) inflammation such as arthritis; (4) pain; (5) skin conditions such as psoriasis and the like; and (6) cardiovascular conditions such as angina and the like.

DETAILED DESCRIPTION

The following reaction schemes illustrate the stereoselective preparation of several leukotriene antagonists in accordance with the method of the present invention. In these reaction schemes standard abbreviations are used. For example, Me for methyl, Et for ethyl, n-Pr for n-propyl, EtOAc for ethyl acetate, MEK for methyl ethyl ketone, KHMDS for potassium hexamethyldisilazane, THF for tetrahydrofuran, DiBAL-H for di-isobutylaluminum hydride, Δ for heating, TFA for trifluoroacetic acid, mCPBA for metachloroperbenzoic acid, p.s.i. for pounds per square inch.

Scheme I (a) Preparation of lactones 5 and 5a:

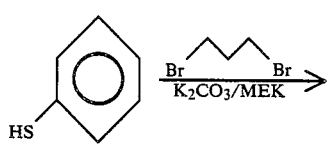

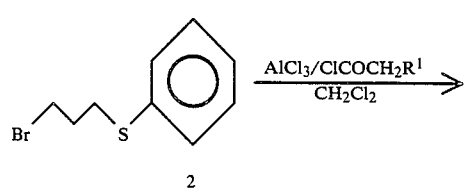

-continued
Scheme I

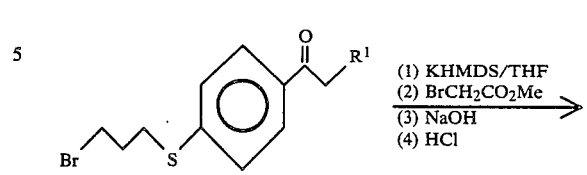

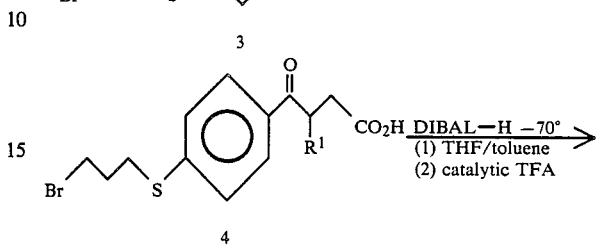

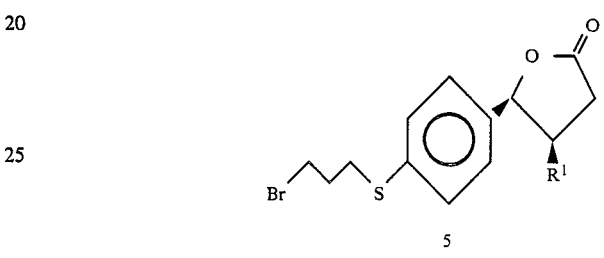

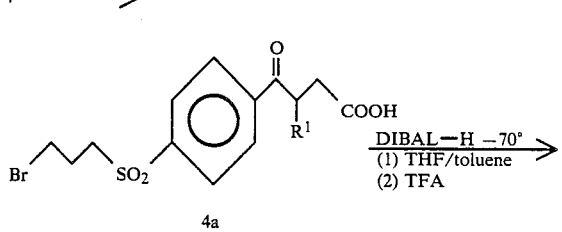

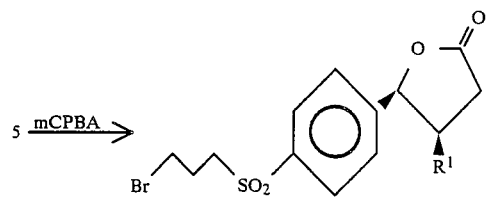

(b) Preparation of 3-propyl-2,4-dihydroxyacetophenone 9:

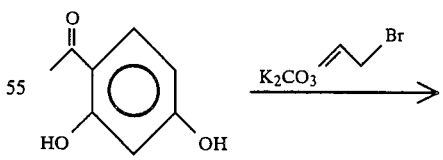

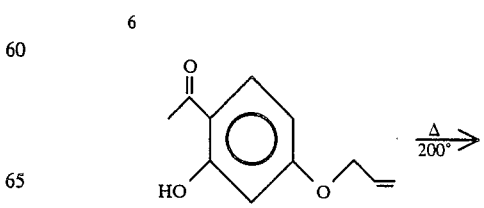

-continued
Scheme I

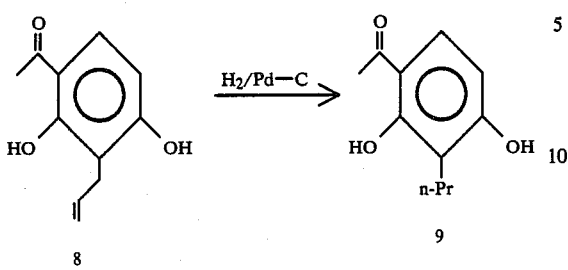

8 → 9

(c) Coupling:

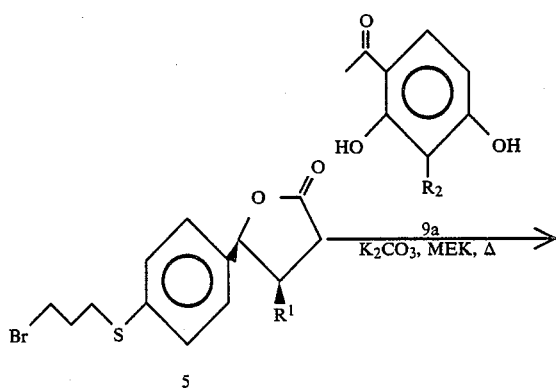

5

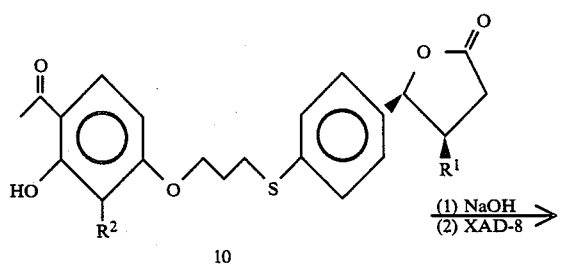

10

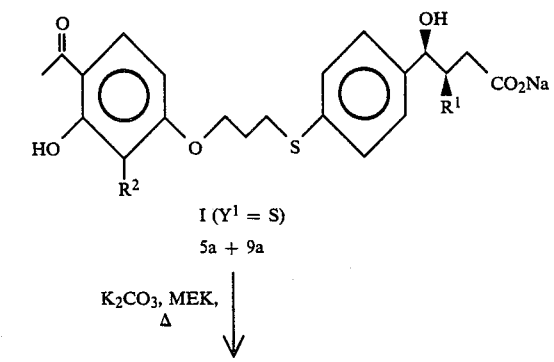

I (Y¹ = S)
5a + 9a

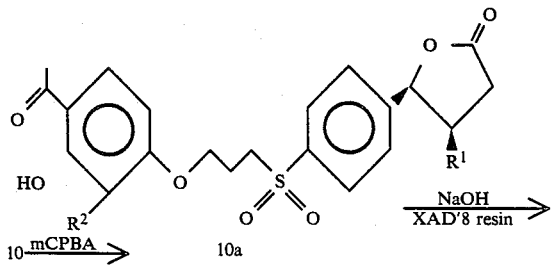

10 —mCPBA→ 10a

-continued
Scheme I

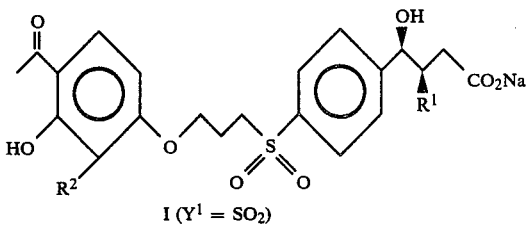

I (Y¹ = SO₂)

In words relative to Scheme I, thiophenol is reacted in MEK or similar inert solvent with excess 1,3-dibromopropane and a weak anhydrous base such as $K_2CO_3$ to give compound 2. 2 is reacted with an alkanoic acid chloride in a solvent such as $CH_2Cl_2$ (or $CH_3NO_2$ or other inert solvent) in the presence of a Lewis acid such as $AlCl_3$ to give 3. 3 is reacted in a dry solvent such as THF (or ether) with a hindered strong base, such as KHMDS (or K di-isopropylamide, etc.) at low temperature. The resulting enolate anion is reacted with methyl bromoacetate at low temperature to give 4. 4 is stereoselectively reduced by the reaction of DiBAL-H in a mixture of THF-toluene at low temperature, followed by acid catalyzed lactonization with an acid such as TFA in less than an equivalent, to give 5 contaminated with small amounts of its (5R*, 4R*)diastereomer. The lactone 5 is reacted with phenol 9a in a solvent such as MEK with a weak base such as $K_2CO_3$ under reflux to give 10. 10 may be further purified by swishing in ether to remove small amounts of isomeric impurities. 10 is hydrolyzed with sodium hydroxide in a homogeneous mixture of water, THF and methanol. The mixture is concentrated to remove non-aqueous solvents then excess base is removed by adsorbing on XAD-8 resin, washing with water then eluting with ethanol to give I (Y¹=S) as its sodium salt.

Also, 4 can be oxidized to a sulfone derivative with the action of an oxidizing agent such as m-chloroperbenzoic acid or peracetic acid to give 4a. 4a is reduced in an analogous manner to 5a, and similarly converted to 10a and to I (Y¹SO₂).

In the DIBAL-H reduction of 4 or 4a some improvement in stereoselectivity can be further realized by the addition of about 1 equivalent of anhydrous $ZnCl_2$ to the mixture prior to addition of the reducing agent. Thus, treatment of 4 (or 4a) with 1.1 equivalents of zinc chloride, then with 2.25 equivalents of DIBAL-H at −80° to −30° C. produces 5 (or 5a) in greater than 98.5% isomeric purity.

Thus, an embodiment of this invention is the process of reducing a compound of structure 4 or 4a which comprises treating 4 or 4a with about 1.1 equivalents of $ZnCl_2$ and then with about 2.25 equivalents of DIBAL-H at −80° to −30° C. in a mixture of THF-toluene to produce, after pH adjustment with a mineral acid (such as HCl), the free acid, followed by acid catalyzed lactonization with less than one equivalent of a mild acid. Preferably, lactonization is brought about by gentle warming (30° C.-60° C.) of the free acid in a suitable solvent such as toluene, in the absence of added acid.

Scheme II

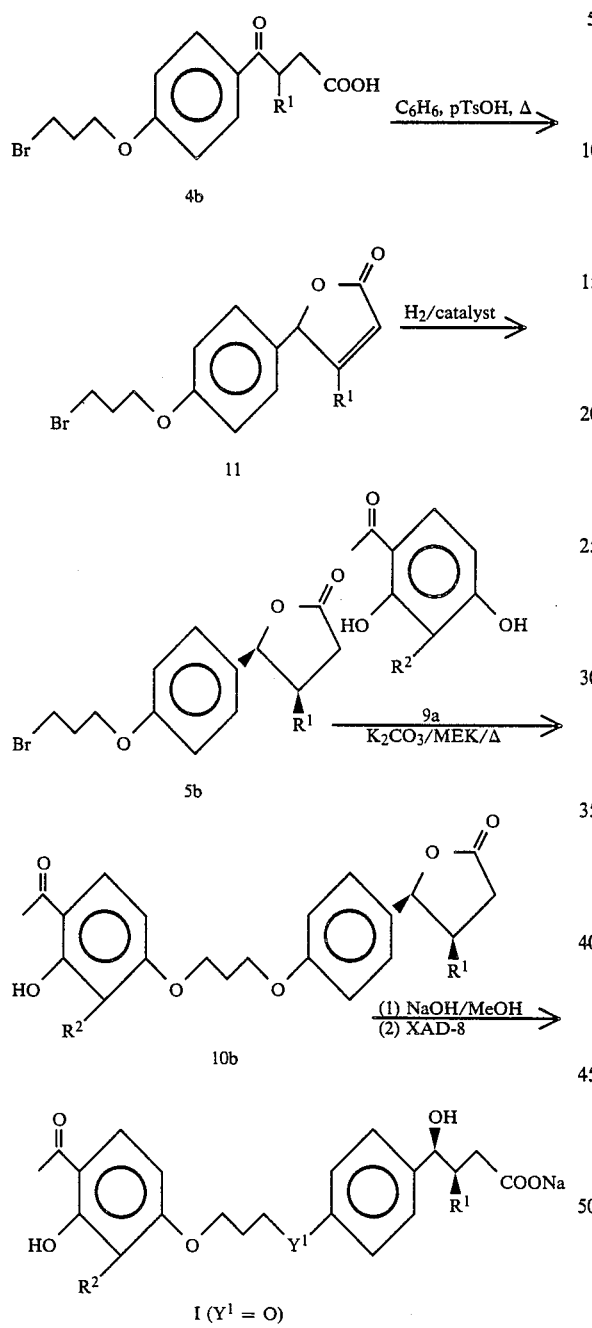

Scheme III

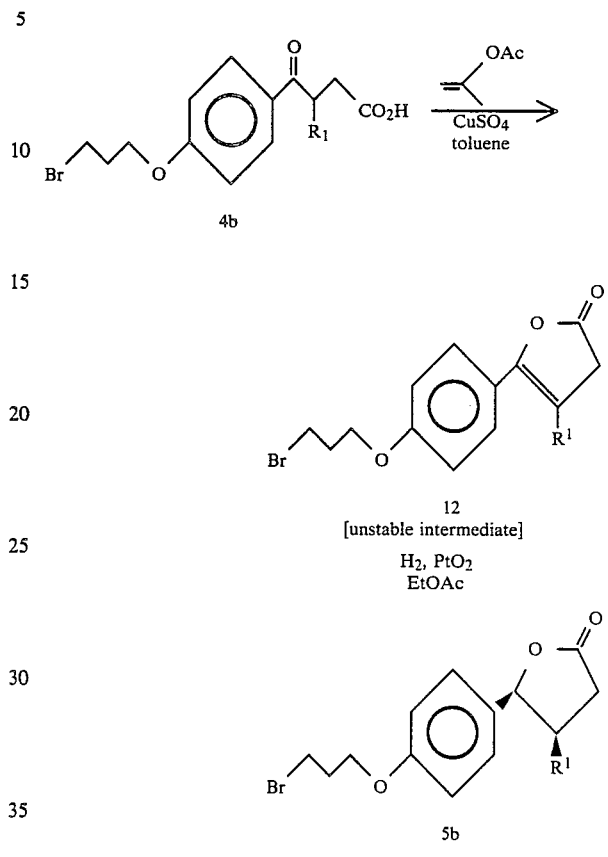

In words relative to Scheme III, the keto acid 4b is dehydrated under weakly Lewis acidic conditions such as with copper sulfate and isopropenylacetate to give the enollactone 12, which is rapidly hydrogenated (before it has the chance to isomerize to 11) with $H_2$ and a catalyst such as $PtO_2$ in a solvent such as EtOAc to give the lactone 5b, essentially free of contamination with the 5R*, 4R* diastereomer.

In words relative to Scheme II, the keto-acid 4b is dehydrated under acidic conditions (such as azeotropic dehydration with benzene or toluene, reflux, water separator with p-toluenesulfonic acid or such strong acid to the enelactone 11. 11 is hydrogenated with a catalyst such as $Pt_2O$ or $(Ph_3P)_3PhCl$ in ethyl acetate or ethanol to give the lactone 5b contaminated with small amounts of the 5R*, 4R* diastereomers. 5b is converted, in a manner analogous to that of Scheme I to the sodium salt, I ($Y^1 = O$).

Scheme IV

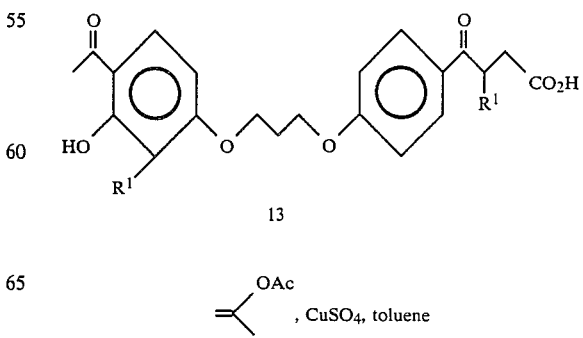

-continued
Scheme IV

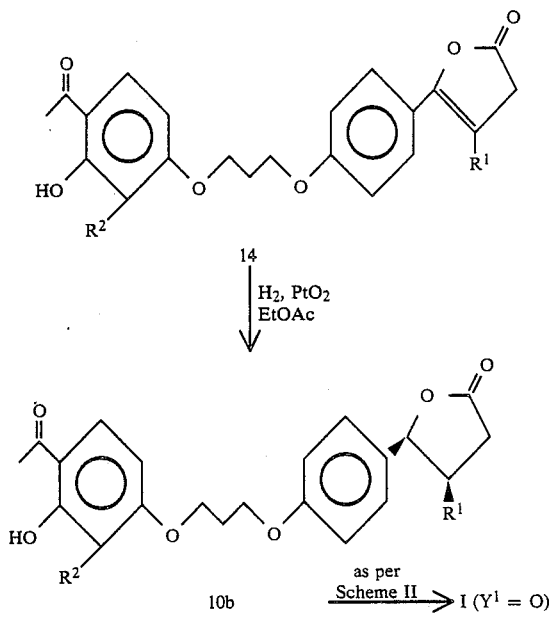

In words relative to Scheme IV, compound 13 is dehydrated to compound 14 under conditions similar to those for the conversion of 4b into 12 (Scheme III). Hydrogenation of 14 under conditions similar to those described for Scheme III gave 10b, which was converted to I ($Y^1$=O) as indicated in Scheme II.

An embodiment of this invention is a compound of the formula

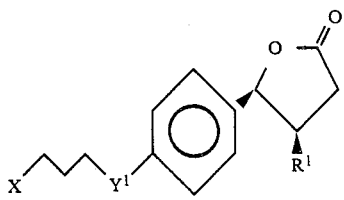

wherein:
$Y^1$ is O, S or $SO_2$;
$R^1$ is $C_1$ to $C_6$ alkyl;
$R_2$ is $C_1$ to $C_6$ alkyl;
X is Br or

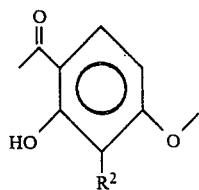

The following examples illustrate the present invention without, however, limiting the same thereto. All temperatures are expressed in degrees Celsius.

EXAMPLE 1

Preparation 3-Bromopropylphenylsulfide

Powdered anhydrous potassium carbonate (4.3 kg, 31 moles) was added to a mixture of 1,3-dibromopropane (6.55 kg, 32 moles), thiophenol (1.2 kg, 10.9 moles) and methylethylketone (9 L). Within 30 minutes the mixture had generated enough heat to attain reflux. Reflux was then maintained for another 30 to 60 minutes. The mixture was permitted to come to room temperature overnight. The solvent layer was siphoned off and filtered through celite. The salts were filtered and washed with acetone. The filtrates were concentrated. The residue was vacuum distilled. Three fractions were collected:
1. b.p. 45° C. at 0.5 mm—1,3-dibromopropane
2. b.p. 105°–110°C. at 0.5 mm—3-bromopropylphenyl sulfide
3. b.p. 184° C. at 0.7 mm—1,3-diphenyldithiopropane
Anal. Calcd for $C_9H_{11}SBr$:
C, 46.76; H, 4.79; S, 13.87; Br, 34.56.
Found: C, 46.22; H, 4.48; S, 13.89; Br, 34.20.

EXAMPLE 2

Preparation of 4-(3-Bromopropylthio)phenylpropan-1-one

To a solution of thioether from Example 1, (460 g, 2 moles) and propionyl chloride (202 g, 2.2 moles) in dichloromethane (8 L) at −15° C. was added in portions of approximately 30 g over 1 hour, aluminum chloride (320 g, 2.4 moles). After two hours at −15° C. the reaction mixture was quenched with ice until it became colorless. 1N HCl (2 L) was added and the reaction mixture was stirred until two clear phases were obtained (approximately 30 minutes). The organic layer was siphoned off and dried ($Na_2SO_4$). Evaporation afforded an oil which crystallized upon addition of hexane (2 L) and cooling in ice water bath; yield 470 g, m.p. 40°–41° C.

EXAMPLE 3

Preparation of 4-(3-Bromopropylthio)benzene-β-methyl-γ-oxobutanoic acid

To a solution of KHMDS (4.96 moles) in toluene (8 L) (Note 1) and THF (8 L) (Note 2) at −78° C. (Note 3) under $N_2$ was added dropwise the ketone from Example 2 (1.36 kg, 4.8 moles) in THF (1500 ml) over 2½ hours. The reaction mixture was stirred 1 hour at 78° C. Methyl bromoacetate (520 ml, 5.6 moles) in THF (800 ml) was added dropwise over 1½ hours. After stirring 1 hour at −78° C. the reaction mixture was poured with stirring into 16 L of HCl (1N). The organic layer was separated and the aqueous layer was further extracted with ethyl acetate (4 L). The combined organic layers were evaporated. The residue was dissolved in a mixture of THF (6 L) and EtOH (6 L), and NaOH (3 L, 2.6M) was added. After stirring 2 hours at room temperature the homogenous reaction mixture was concentrated under vacuo to remove THF and EtOH (Note 4). The aqueous residue was extracted with ethyl acetate (2×2 L). The aqueous layer was cooled in ice-water and acidified with concentrated HCl (approximately 800 ml). Extraction with ethyl acetate (Note 5) (1×4 L, 1×1 L), drying ($Na_2SO_4$) and evaporation afforded the title acid 1.360 kg as a tan oily solid, m.p. 92°–96° C., which was used as is in Example 4.

Notes
1. Potassium hexamethyldisilazane (KHMDS) in toluene obtained from Callery Chemical Co., Callery, Pa.
2. Aldrich 99.9% or 99.5% THF was used as received.
3. Dry-ice ethanol bath.

4. All THF and EtOH must be removed in order to get clean separation of phases in the extraction. Co-evaporation of the residue with 4 L ethyl acetate is necessary in some cases.
5. In some runs the product precipitated.

EXAMPLE 4

Preparation of cis-4-(3-Bromopropylthio)phenyl-3-methylbutyrolactone

To a solution of the keto acid from Example 3 (380 g, 1.1 moles) in THF (7 L) (Note 1) at −78° C. under $N_2$ was added dropwise over 3 hours DiBAL-H (1.8 L of 25% solution in toluene) (Note 2). After stirring 1 hour at −78° C. the cold reaction mixture was poured into 1.5N HCl (8 L). The organic layer was separated and the aqueous layer was extracted with ethyl acetate (2 L). The combined organic layers were dried ($Na_2SO_4$) and evaporated in vacuo. The residue was dissolved in $CH_2Cl_2$ (1.5 L) and TFA (3 ml) (Note 5) was added. After stirring overnight at room temperature the reaction mixture was evaporated, dissolved in $Et_2O$ (1.5 L) washed with 1N $NaHCO_3$ (2×800 ml), dried ($Na_2SO_4$) and evaporated. Purification on flash silica gel (Note 4) (230–400 mesh, 1 kg) using 10:3 hexane/ethyl acetate as eluant afforded 230 g of the lactone as a slightly yellow oil (Note 3). NMR ($CDCl_3$) δ 0.7 (d, 3H), 2.0–2.5 (m, 2H), 2.7–3.2 (m, 2H), 3.5 (t, 1H), 5.55 (d, 1H), 7.1 (d, 2H), 7.35 (d, 2H).

Notes
1. Commercial THF 99.9% or 99.5% obtained from Aldrich was used as received.
2. Aldrich, 2 bottles, must be in toluene to obtain optimum ratio.
3. Contaminated with approximately 7–10% the trans-isomer.
4. A filtration to remove polar impurities.
5. Excess TFA or longer treatment can lead to larger amounts of trans-isomer.

EXAMPLE 5

Preparation of 4-Allyloxy-2-hydroxyacetophenone

Allyl bromide (1.25 L, 14.5 moles) was poured into a stirring mixture of 2,4-dihydroxyacetophenone (2 kg, 13.2 moles), milled potassium carbonate (2.6 kg, 19.1 moles) and anhydrous acetone (7 L). The mixture was refluxed for 3 hours, cooled and filtered.

The filtrate was concentrated to obtain a brown oil (2.5 kg) which was dissolved in dischloromethane (2.5 L). The solution was passed through silica gel (1.5 kg) contained in a sintered disc funnel. Another portion of dichloromethane (4 L) was used to wash the product off the silica gel. The eluates were combined, dried ($Na_2SO_4$) and concentrated well under vacuum. The title compound thus obtained was used directly in the next step.

EXAMPLE 6

Preparation of 3-Allyl-2,4-dihydroxyacetophenone

4-Allyloxy-2-hydroxyacetophenone from Example 5 (1 kg, 5.22 moles) was heated under $N_2$ atmosphere for 3 hours. The internal temperature was maintained between 195–205° C. (Notes 1, 2, 3). The reaction mixture was cooled to 80–90° C. and carbon tetrachloride (2 L) was added slowly through the top of a condenser (Note 4). The mixture was stirred and refluxed for 30 minutes. The heterogeneous mixture was slowly brought to room temperature and left to crystallize overnight. The solid was filtered and washed with some carbon tetrachloride. m.p. 133°–134° C.

Notes
1. The reaction was carried out in a 5 liter flask equipped with a mechanical stirrer and 2 reflux condensers. The external oil bath temperature of 210° C. was attained using a hot plate and a 500 watt-115 volt oil heating booster.
2. The time and temperature are extremely crucial. Internal cyclization of the rearranged product to 2,3-dihydro-2-methyl-4-hydroxy-5-acetyl benzofuran or decomposition occurs rapidly at higher temperatures. Lower temperatures and longer heating periods give lower yields of product. The reaction was monitored by TLC every 30 minutes using 15% ethyl acetate-hexane eluent.
3. The reaction can also be performed using a heating mantle and using a thermo-regulator to regulate the inside temperature to 195° C.
4. An improved procedure is to pour the reaction mixture (at approximately 100° C.) into 3 L of chloroform and allow it to crystallize at 5° C. overnight.

EXAMPLE 7

Preparation of 3-Propyl-2,4-dihydroxyacetophenone

A mixture of 3-allyl-2,4-dihydroxyacetophenone from Example 6 (250 g, 1.31 moles) ethyl alcohol (1 L) and 5% palladium on carbon (5 g) was hydrogenated for 2 hours at room temperature using a Parr hydrogenator (Note 1). The catalyst was filtered off on celite and the filtrate was concentrated.

The residual solid was powdered and swished for 2 hours at room temperature using 5 ml of 5% ethyl acetate-hexane per 1 gram of product to give the title compound. m.p. 126°–128° C. (Note 2), sufficiently pure for use in the next step.

Notes
1. The samples were analyzed by TLC and NMR. Sometimes 10–15% isomerization may occur and continuing hydrogenation with fresh catalyst for an extra 15 minutes will process the slower hydrogenating isomer (NMR) to the desired product.
2. Recrystallization from chloroform 300 g/2 L serves to purify the product if necessary.

EXAMPLE 8

Preparation of (βS, γR) and (βR, γS)-4-((3-(4-acetyl-3-hydroxy-2-propyl(phenoxy)-propyl)thio)-γ-hydroxy-β-methylbenzenebutyric acid lactone A solution of the lactone from Example 4 (190 g, 0.58 mole), powdered $K_2CO_3$ (240 g, 1.74 mole) (Note 1) and the phenol from Example 7 (112 g, 0.58 mole) in methyl ethyl ketone (2 L) was refluxed under $N_2$ with stirring for 4 hours. The reaction mixture was cooled, filtered through a pad of celite and the filter cake was washed with $CH_2Cl_2$ (500 ml). The filtrate was evaporated to give a dark oil. Chromatography of the residue on silica gel (1.0 kg, 230–400 mesh) (Note 2) using from 10:3 hexane/ethyl acetate to 10:7 hexane/ethyl acetate afforded the coupled product, 218 g (85%) as a yellow solid. The finely powdered solid was swished with ether (1 L) overnight and filtered. This process was repeated 5 times with ether (2 L) to yield 165 g of the title compound as a white solid; m.p. 95°–96° C.

Notes
1. $K_2CO_3$ must be milled through a fine mesh.
2. Sample should be applied to column in 100 ml $CH_2Cl_2$ and 100 ml eluting solvent to avoid crystallization on the column.

EXAMPLE 9

Preparation of Sodium (βS, γR) and (βR, γS)-4-((3(4-acetyl-3-hydroxy-2-propyl(phenoxy)-propyl)thio)-γhydroxy-β-methylbenzenebutanoate To a solution of the lactone from Example 8 (250 g, 0.57 moles) in THF (1.6 L) and MeOH (350 c.c.) was added 2N NaOH (340 ml, 0.68 moles). The reaction was stirred overnight at room temperature under $N_2$. The mixture was concentrated at 40° C. in an efficient rotary evaporator to a thick oil. All traces of methanol were removed in vacuo. One quarter of the residue was dissolved in a minimum of water (approximately 100 ml) and applied to a column of XAD-8 (1.5 kg) (Note 1). After 1 hour the column was eluted with $H_2O$ (200 ml).

One hour later the column was eluted with H$_2$O (6 L) to remove excess NaOH. At this point the pH of the effluent was about pH 8–9, further washing leads to partial ion exchange and the absorbed salt is converted to the free acid. The column was then eluted with EtOH (4 L). This process was repeated with the other 3 portions of crude sodium salt. The combined EtOH fractions were evaporated at 45° C. in a rotary evaporator. The residue was coevaporated with EtOH and dried under high vacuum (5 days at 0.1 mm) to yield the sodium salt as a beige foam. 250 g (Note 2).

Anal. Calcd. for C$_{25}$H$_{36}$O$_6$ Na: C, 62.22; H, 6.48; S, 6.64. Found: C, 62.10; H, 6.45; S, 6.49.

Notes
1. Commercial XAD-8 (Sigma) was purified before using by washing with CH$_2$Cl$_2$ (8 L/kg), PrOH (8 L/kg), MeOH (8 L/kg) and finally with H$_2$O (20 L/kg).
2. The foam is hygroscopic and must be kept in a sealed container in a desiccator.

EXAMPLE 10

Preparation of 5-(4-(3-Bromopropyloxy)phenyl)-4-methyl-2-oxo-2,5-dihydrofuran 4-(3-Bromopropyloxy)-γ-oxo-β-methylbenzenebutanoic acid (30 g) in toluene (300 ml) was refluxed with p-toluenesulfonic acid (500 mg) under a Dean-Stark water separator for 18 hours. The mixture was filtered through basic alumina (20 g). The alumina was further washed with ethyl acetate and the combined eluants were reduced to dryness to provide the title compound as an oil.

NMR (CDCl$_3$) δ 1.9 (3H, m), 2.35 (2H, m), 3.60 (2H, t), 4.12 (2H, t), 5.67 (1H, broad s), 5.95 (1H, m), 6.92 (2H, d), 7.15 (2H, d).

EXAMPLE 11

Preparation of (5R, 4S) and (5S, 4R)-5-(4-(3-bromo-propyloxy)phenyl)-4-methyl-2,3,4,5-tetrahydrofuran-2-one The lactone from Example 10 (26 g) was hydrogenated in ethyl acetate (200 ml) over PtO$_2$ (1 g) at 20 p.s.i. H$_2$ pressure for 30 minutes. The mixture was filtered, concentrated and the residue was purified by chromatography on silica gel to Provide the title compound as an oil, contaminated with 7% of the (5S, 4S), (5R, 4R) diastereomer as determined by NMR spectroscopy.

NMR (CDCl$_3$) δ 0.63 (2.8H, d), 1.1 (0.2H, d), 2.1–2.9 (5H, m), 3.55 (2H, t), 4.05 (2H, t), 4.85 (0.07H, d), 5.55 (0.93H, d), 6.8–7.25 (4H,m).

The residual (5S, 4S), (5R, 4R)-diastereomers could be removed by careful chromatography on silica gel to provide the pure title compound.

EXAMPLE 12

Stereoselective preparation of (5R, 4S) and (5S, 4R)-5(4-(3-bromopropyloxy)phenyl)-4-methyl-2,3,4,5-tetra-hydrofuran-2-one A mixture of 4-(3-bromopropyloxy)-γ-oxo-β-methylbenzenebutanoic acid (50 g), anhydrous cupric sulfate (50 g), isopropenyl acetate (200 ml) and toluene (200 ml) was refluxed in an atmosphere of nitrogen for 30 minutes during which about 150 ml of the distillate was collected. The mixture was cooled, diluted with ethyl acetate (150 ml) and filtered through a bed of Celite. The solid was washed with ethyl acetate (150 ml) and the combined filtrates were washed with saturated NaHCO$_3$ (100 ml×4), brine (100 ml×2) and dried over Na$_2$SO$_4$. The organic layer was concentrated and the residue was dissolved in ethyl acetate (about 300 ml). Platinum oxide (PtO$_2$) (3.0 g) was added and the cooled (about 10° C.) mixture was hydrogenated at 20 p.s.i. H$_2$ pressure for 90 minutes. The mixture was filtered, concentrated and the residue was purified by (suction) chromatography on silica gel to provide the title compound as an oil, uncontaminated with the (5S, 4S) and (5R, 4R) diastereomers as determined by NMR.

EXAMPLE 13

Preparation of (5R, 4S) and (5S, 4R)-5-(4-(3-(4-acetyl-3-hydroxy-2-propylphenyloxy)-propyloxy)phenyl)-4-methyl-2,3,4,5-tetrahydrofuran-2-one The bromide from Example 12 (4.5 g, 14.4 mmol) was reacted with 2,4-dihydroxy-3-propylacetophenone (2.9 g, 15.0 mmol) in methyl ethyl ketone (45 ml) containing anhydrous K$_2$CO$_3$ (4.0 g, 29.0 mmol) at reflux temperature for 6 hours in an atmosphere of nitrogen. The mixture was filtered, concentrated in vacuo and the residue was purified by chromatography on silica gel to provide the title compound, m.p. 88.5°–89.5° C.

Anal. Calcd. for C$_{25}$H$_{30}$O$_6$: C, 70.40; H, 7.09. Found: C, 70.16; H, 7.10.

EXAMPLE 14

Preparation of Sodium 4-(3-(4-acetyl-3-hydroxy-2-propylphenoxy)propyloxy)-γ-hydroxy-β-methylbenzenebutanoate The lactone from Example 13 (3.0 g, 7.0 mmol) was hydrolyzed with 1N NaOH (10.5 ml), methanol (1 ml) and THF (15 ml) at room temperature for 15 hours. The mixture was concentrated and the residue was Purified by chromatography on XAD-8 to provide the title compound as a foam.

Anal. Calcd. for C$_{25}$H$_{31}$O$_7$Na:
C, 64.36; H, 6.70.
Found: C, 64.18; H, 7.04.

EXAMPLE 15

Alternative preparation of (5R, 4S) and (5S, 4R)-5-(4(3-(4-acetyl-3-hydroxy-2-propylphenyloxy)-propyloxy)-phenyl)-4-methyl-2,3,4,5-tetrahydrofuran-2-one Following the procedure of Example 12 but substituting 4-(3-(4-acetyl-3-hydroxy-2-propylphenyloxy)-Propyloxy)-γ-oxo-β-methylbenzenebutanoic acid for 4-(3-bromopropyloxy)-γ-oxo-β-methylbenzenebutanoic acid, the title compound was obtained as an oil, uncontaminated with the (5S, 4S) and (5R, 4R) diastereomers as determined by NMR spectroscopy.

EXAMPLE 16

Preparation of cis-4-(3-Bromopropylthio)phenyl-3-methylbutyrolactone

Step A: Preparation of Anhydrous Solutions of Zinc Bromide and Zinc Chloride in Tetrahydrofuran Zinc Bromide Anhydrous zinc bromide (153 g, Alfa) was added to a dry 0.5-liter volumetric flask equipped for magnetic stirring. Tetrahydrofuran (water content: 0.02 mg H$_2$O/mL) was added, adjusting the total volume to 450 mL. The mixture was stirred for 40 minutes to complete dissolution. The heat of solution increased the temperature to 40° C. After cooling to 20° C, the volume was adjusted to 0.5 liter with tetrahydrofuran. The water content of the solution was 6.6 mg H$_2$O/mL.

Molecular sieves (175 g, 4A beads, 10–16 mesh) were added and the mixture periodically agitated over 12 hours. The resulting clear, colorless solution of zinc bromide had a calculated molarity of 1.33 (corrected for the original water content of the zinc bromide) and a water content of 0.6 mg H$_2$O/mL. Upon aging over sieves for 5 days the water content of the solution decreased to 0.07 mg H$_2$O/mL. A bromide ion concentration of 2.71 molar was determined by titration with silver nitrate.

Zinc Chloride

In a similar fashion to the above described procedure, 1 liter of a tetrahydrofuran solution of zinc chloride (184 g, 97 minimum assay) was prepared. The water content of the solution prior to sieve drying was 5.1 mg H$_2$O/mL. Reagent grade zinc chloride (97% minimum assay) contained insoluble impurities that produced a milky suspension. This settled upon standing.

Drying over molecular sieves (250 g, 4A beads, 10–16 mesh) produced a clear, colorless solution with a calculated molarity of 1.31 (corrected for the original water content of the zinc chloride) and a water content of 0.5 mg H$_2$O/mL. A chloride ion concentration of 2.65 molar was determined by titration with silver nitrate.

Anhydrous zinc chloride solutions which had been aged at 20° C. for 10 days show no evidence of tetrahydrofuran decomposition by $^{13}$C NMR analysis.

Step B: Preparation of cis-4-(3-bromopropylthio)-phenyl-3-methylbutryolactone

A dry nitrogen-purged 1-liter round-bottomed flask was charged with 4-(3-bromopropylthio)benzene-β-methyl-γ-oxobutanoic acid (50.0 g, 0.145 mole) and sieve-dried tetrahydrofuran (500 mL). The solution was cooled to −20° C., and an anhydrous solution of zinc chloride in tetrahydrofuran (125 mL, 0.164 mole, 1.31M) was added. After cooling to −77° C. a solution of diisobutyl aluminum hydride in toluene (220 mL, 0.33 mole, 5M) added over 0.5 hours maintaining a temperature of −60° C. during the addition. The mixture was warmed to −35° C. over 0.25 hour then aged at that temperature for 0.5 hour.

The reaction mixture was quenched into a well-stirred mixture of 2N aqueous hydrochloric acid (750 mL) and ice (250 g) maintaining a temperature range between 0° to 12° C. during the addition.

The aqueous mixture was twice extracted with ethyl acetate (2×250 mL). The combined organic extract was washed twice with water (2×500 mL.) (Note 1).

The organic extract was dried over sodium sulfate, filtered, and concentrated in vacuo (bath temperature 40° C.) to yield 4-(3-bromopropylthio)-benzene-β-methyl-γ-hydroxybutanoic acid as a yellow oil. The oil was dissolved in toluene (250 mL) and heated at 40°50° C. for 12 hours, periodically removing small portions (25 mL) of the solvent under vacuum.

The course of lactonization was followed by high performance liquid chromatography (HPLC). Once the lactonization was complete, the solution was concentrated and filtered through a short column containing silica gel (100 g, E. Merck Kieselgel-60, 70–230 mesh). The column was first rinsed with hexane to remove toluene, then it was eluted with methylene chloride, collecting the title compound as a yellow oil after concentration. NMR analysis ($^1$H, 250 MHz) indicated contamination by less than 1.5% of the trans-isomer.

Note 1
The pH of the final aqueous wash should be 3.4 in order to insure that no isomerization occurs during the lactonization. Additional water washes are carried out if the pH is below 3.4 until it reaches this value.

What is claimed is:

1. A method of preparing the compound I:

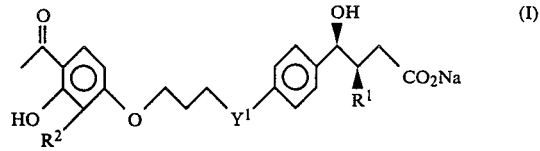

wherein Y$^1$ is O, S or SO$_2$ and R$^1$ and R$^2$ are independently C$_1$–C$_6$ alkyl which comprises:
 (a) stereoselectively reducing a compound of structure 4 to give the lactone 5;
 (b) reacting the lactone 5 with a phenol 9a to give 10;
 (c) hydrolyzing 10 to give the compound I:

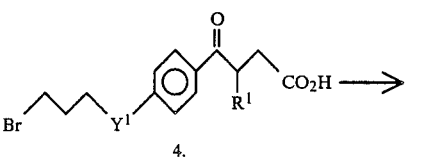

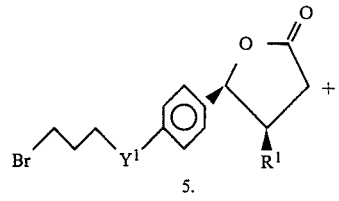

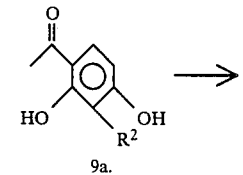

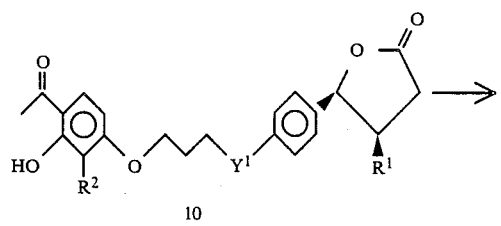

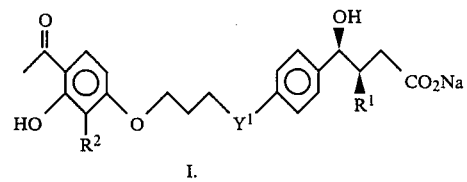

2. A method according to claim 1, wherein R$^1$ is methyl, R$^2$ is n-propyl, and Y$^1$ is S.

3. A method of claim 1 wherein the reduction of step (a) comprises treating a compound of structure 4 with about 1.1 equivalents of zinc chloride and then with about 2.25 equivalents of DIBAL-H at −80° to −30° C. in a mixture of THF-toluene, followed by pH adjustment and heating to 30°–60° C.

* * * * *